United States Patent [19]

Buendia et al.

[11] 4,264,623
[45] Apr. 28, 1981

[54] β-LACTONES OF 2-HYDROXY-CYCLOPENTANE-CARBOXYLIC ACIDS

[75] Inventors: Jean Buendia, Le Perreux-sur-Marne; Michel Vivat, Lagny-sur-Marne; Laurent Taliani, Pavillons-sous-Bois, all of France

[73] Assignee: Roussel Uclaf, Paris, France

[21] Appl. No.: 94,771

[22] Filed: Nov. 16, 1979

[30] Foreign Application Priority Data

Dec. 5, 1978 [FR] France .............................. 78 34183

[51] Int. Cl.³ ...................... C09B 23/16; C09B 23/08; C07D 305/14; A61K 31/365
[52] U.S. Cl. ................. 424/279; 260/343.21; 542/426; 542/429; 542/430; 542/431; 560/122; 562/504
[58] Field of Search ............... 542/426, 429, 430, 431; 260/343.21, 343.3 P; 424/279

[56] References Cited

U.S. PATENT DOCUMENTS

| 4,024,179 | 5/1977 | Bindra et al. | 260/343.3 P |
| 4,113,766 | 9/1978 | Hess | 260/343.3 P |

FOREIGN PATENT DOCUMENTS 2279390 2/1976 France .
2344285 10/1977 France .

*Primary Examiner*—Henry R. Jiles
*Assistant Examiner*—Jane T. Fan
*Attorney, Agent, or Firm*—Hammond, Littell, Weissenberger and Muserlian

[57] ABSTRACT

Novel β-lactones of 2-hydroxy-cyclopentane-carboxylic acids of the formula

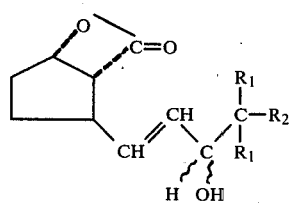

wherein $R_1$ is selected from the group consisting of hydrogen and methyl and $R_2$ is selected from the group consisting of —$CH_2$—O—$CH_2$—$CH_3$ and —X—Ar, X is selected from the group consisting of —O— and —$CH_2$—, Ar is an optionally substituted member selected from the group consisting of thienyl, thiazolyl, phenyl and thiadiazolyl, the optional substituents being at least one member selected from the group consisting of halogen and —$CF_3$ and thw wavy lines indicate that the groups may be in the α, β or β, α-positions or mixtures thereof having hypotensive activity and their preparation.

21 Claims, No Drawings

β-LACTONES OF 2-HYDROXY-CYCLOPENTANE-CARBOXYLIC ACIDS

STATE OF THE ART

French Pat. No. 2,279,390, Netherlands application Ser. No. 76-05856 and copending commonly assigned U.S. patent application Ser. No. 036,877 filed May 8, 1979 which is a continuation of application Ser. No. 779,178 filed Mar. 18, 1977 describe similar compounds.

OBJECTS OF THE INVENTION

It is an object of the invention to provide the novel lactones of formula I and a novel process and novel intermediates for their preparation.

It is another object of the invention to provide novel hypotensive compositions and to provide a novel method of reducing blood pressure in warm-blooded animals.

These and other objects and advantages of the invention will become obvious from the following detailed description.

THE INVENTION

The novel β-lactones of the invention are β-lactones of 2-hydroxy-cyclopentane-carboxylic acids of the formula

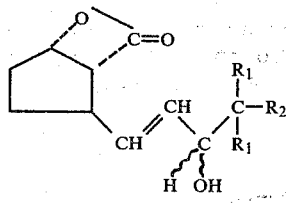

wherein $R_1$ is selected from the group consisting of hydrogen and methyl and $R_2$ is selected from the group consisting of —$CH_2$—O—$CH_2$—$CH_3$ and —X—Ar, X is selected from the group consisting of —O— and —$CH_2$—, Ar is an optionally substituted member selected from the group consisting of thienyl, thiazolyl, phenyl and thiadiazolyl, the optional substituents being at least one member selected from the group consisting of halogen and —$CF_3$ and the wavy lines indicate that the groups may be in the α,β or β,α-positions or mixtures thereof.

Examples of suitable substituents on the group Ar are at least one fluorine, chlorine, bromine, iodine and/or trifluoromethyl. Among the preferred compounds of formula I are those wherein $R_2$ is thien-3-yloxy, thiazol-2-yloxy, 1,2,5-thiadiazol-3-yloxy, phenyloxy or ethoxymethyl.

Specific preferred compounds of formula I are the lactone of (1RS, 2SR, 5RS, 3'SR)(1'E) 2-hydroxy-5-[3'-hydroxy-4'-(3''-thienyloxy)-1'-butenyl]-cyclopentane-1-carboxylic acid, the lactone of (1RS, 2SR, 5RS, 3'RS)(1'E) 2-hydroxy-5-[3'-hydroxy-4'-(3''-thienyloxy)-1'-butenyl]-cyclopentane-1-carboxylic acid, the lactone of (1RS, 2SR, 5RS, 3'RS-3'SR) (1'E) 2-hydroxy-5-[3'-hydroxy-4',4'-dimethyl-6'-oxa-1'-octenyl]-cyclopentane-1-carboxylic acid, the lactone of (1RS, 2SR, 5RS, 3'SR)(1'E) 2-hydroxy-5-[3'-hydroxy-4'-phenoxy-1'-butenyl]-cyclopentane-1-carboxylic acid and the lactone of (1RS, 2SR, 5RS, 3'RS)(1'E) 2-hydroxy-5-[3'-hydroxy-4'-phenoxy-1'-butenyl]-cyclopentane-1-carboxylic acid.

The novel process of the invention for the preparation of the lactones of formula I comprises reacting a compound of the formula

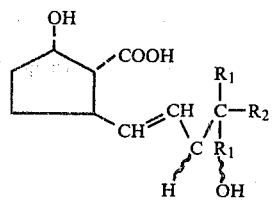

wherein $R_1$ and $R_2$ have the above definition with a reactant selected from the group consisting of tosyl chloride, alkyl chloroformates, dicycloalkylcarbodiimides, dialkylcarbodiimides and thionyl chloride to form a functional acid derivative which reacts with the hydroxyl to form the lactone ring.

In a preferred mode of the said process, the selected reactant is tosyl chloride which forms a mixed anhydride of the acid. The reaction is preferably effected in the presence of an inorganic base such as an alkali metal carbonate or an organic base such as methylmorpholine, pyridine, diazabicyclooctane or a trialkylamine such as triethylamine. Other preferred embodiments include the use of thionyl chloride or an alkyl chloroformate such as isobutylchloroformate in the presence of the said bases.

Another process of the invention for the preparation of the compounds of formula I comprises reacting a compound of the formula

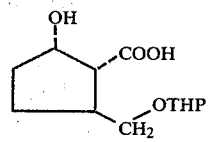

wherein THP is tetrahydropyranyl with a reactant for the formation of a functional acid derivative to obtain a compound of the formula

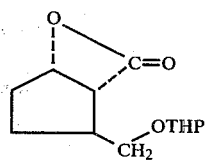

reacting the latter with an acid to form a compound of the formula

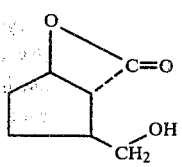

reacting the latter with an oxidation agent to form a compound of the formula

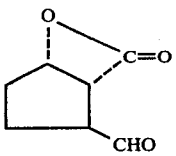

VI reacting the latter in the presence of a strong base with a phosphonate of the formula

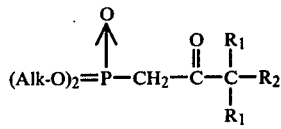

VII wherein $R_1$ and $R_2$ have the above definitions and Alk is alkyl of 1 to 4 carbon atoms to obtain a compound of the formula

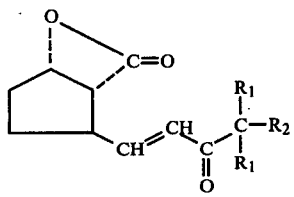

VIII and reacting the latter with a reducing agent to form the corresponding compound of formula I.

In a preferred mode of the said process, the reactant to form the functional acid derivative is the same as the reactant with the compound of formula II, preferably tosyl chloride in the presence of diazabicyclooctane to form the mixed anhydride. The acid is preferably oxalic acid but other acids such as hydrochloric acid, sulfuric acid or acetic acid may be used. The preferred oxidation agent is the complex of chromic oxide in pyridine but chromic oxide in triethylamine or in a collidine may also be used. In the phosphonate of formula VII, Alk is preferably methyl but may be other alkyls such as ethyl, propyl or butyl. The strong base is preferably sodium hydride but other bases such as sodium amide, sodium tert.-amylate or butyllithium may be used. The preferred reducing agent is zinc borohydride but other agents such as sodium borohydride, sodium trismethoxyborohydride or lithium tris(sec-butyl) borohydride may be used.

The compounds of formulae I and II contain a hydroxyl group which may be in one of 2 possible positions, either α- or β- to the carbon atom to which it is attached, or mixtures thereof which may be separated by known physical methods, especially chromatography. The compounds of formula I exist in the form of racemates or optical isomers and the racemates may be separated by the usual methods.

The novel intermediates products of the invention are the compounds of formula II and the compounds of the formula

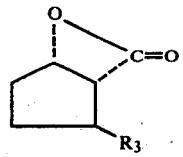

IX wherein $R_3$ is selected from the group consisting of —$CH_2OH$, formyl or tetrahydropyranyloxymethyl.

The compounds of formula II may be prepared by reacting a compound of the formula

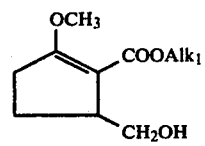

X wherein $Alk_1$ is an alkyl of 1 to 4 carbon atoms with an oxidation agent such as chromic oxide in pyridine to obtain a compound of the formula

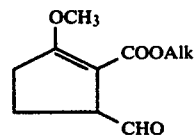

XI reacting the latter with a phosphonate of formula VII in the presence of a strong base such as sodium hydride to obtain a compound of the formula

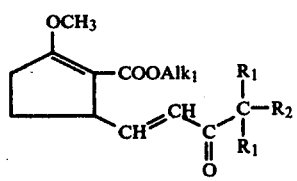

XII reacting the latter with a reducing agent such as zinc borohydride to obtain a compound of the formula

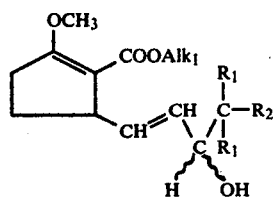

XIII which, if desired may be separated into its isomers, reacting the latter with an acid such as oxalic acid to obtain a compound of the formula

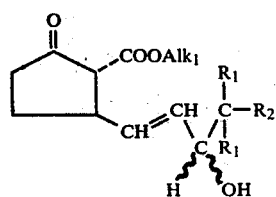

XIV reacting the latter with a reducing agent such as sodium tris (sec-butyl) borohydride to form a compound of the formula

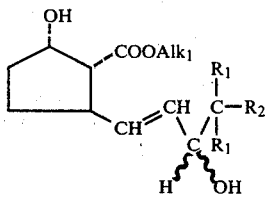

and treating the latter with first a base such as sodium hydroxide and then with an acid such as dilute hydrochloric acid to form the corresponding compound of formula II.

The compounds of formula III may be made by reacting a compound of the formula

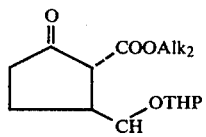

wherein $Alk_2$ is alkyl of 1 to 4 carbon atoms and THP is tetrahydropyranyl with a reducing agent such as sodium tris(sec.-butyl) borohydride to obtain a compound of the formula

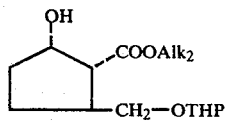

and treating the latter with a base such as sodium hydroxide and then with an acid such as dilute hydrochloric acid to obtain the corresponding compound of formula III. The compounds of formulae X and XVI are described in French Pat. No. 2,332,971.

The novel hypotensive compositions of the invention are comprised of a hypotensively effective amount of at least one compound of formula I and an inert pharmaceutical carrier or excipient. The compositions may be in the form of tablets, dragees, gelules, granules, suppositories or injectable solutions or suspensions.

Examples of suitable excipients are talc, arabic, gum, lactose, starch, magnesium stearate, cacao butter, aqueous and non-aqueous vehicles.

Due to their hypotensive properties, the compositions are useful for treating hypertension and circulation troubles. The preferred compositions of the invention are those wherein $R_2$ is thien-3-yloxy, thiazol-2-yloxy, 1,2,5-thiadiazol-3-yloxy, phenoxy or ethoxymethyl. Especially preferred compositions are those wherein the active ingredient is selected from the group consisting of the lactone of (1RS, 2SR, 5RS, 3′SR)(1′E) 2-hydroxy-5-[3′-hydroxy-4′-(3″-thienyloxy)-1′-butenyl]-cyclopentane-1-carboxylic acid, the lactone of (1RS, 2SR, 5RS, 3′RS)(1′E) 2-hydroxy-5-[3′-hydroxy-4′-(3″-thienyloxy)-1′-butenyl]-cyclopentane-1-carboxylic acid, the lactone of (1RS, 2SR, 5RS, 3′RS-3′SR)(1′E) 2-hydroxy-5-[3′-hydroxy-4′,4′-dimethyl-6′-oxa-1′-octenyl]-cyclopentane carboxylic acid, the lactone of (1RS, 2SR, 5RS, 3′SR)(1′E) 2-hydroxy-5-[3′-hydroxy-4′-phenoxy-1′-butenyl]-cyclopentane-1-carboxylic acid and the lactone of (1RS, 2SR, 5RS, 3′RS)(1′E) 2-hydroxy-5-[3′-hydroxy-4′-phenoxy-1′-butenyl]-cyclopentane-1-carboxylic acid.

The novel method of the invention of reducing blood pressure in warm-blooded animals comprises administering to warm-blooded animals an hypotensively effective amount of at least one compound of formula I. The compounds may be administered orally, rectally, parenterally or locally. The usual daily dose is 0.01 to 40 mg/kg depending on the compound and the method of administration.

In the following examples there are described several preferred embodiments to illustrate the invention. However, it should be understood that the invention is not intended to be limited to the specific embodiments.

EXAMPLE 1

Lactone of (1RS, 2SR, 5RS, 3′RS)(1′E) 2-hydroxy-5-[3′-hydroxy-4′-(3″-thienyloxy)-1′-butenyl]-cyclopentane-1-carboxylic acid

STEP A: Methyl (5RS)(1′E) 2-methoxy-5-[3′-oxo-4′-(3″-thienyloxy)-1′-butenyl]-1-cyclopentene-carboxylate 21 g of anhydrous chromic acid anhydride were added in small amounts at 25°–30° C. to a solution of 33.7 ml of pyridine and 300 ml of methylene chloride and after the mixture stood at room temperature for 15 minutes, 6.5 g of methyl (5RS) 2-methoxy-5-hydroxymethyl-1-cyclopentene-carboxylate were added thereto over 10 minutes. The mixture stood at room temperature for 30 minutes and was then filtered and the filtrate was evaporated to dryness to obtain 4.5 g of an aldehyde.

6.5 g of dimethyl 2-oxo-3-(3′-thienyloxy)-propylphosphonate were dissolved in 100 ml of dimethoxyethane and 1 g of sodium hydride as a 61.5% suspension in oil was added to the solution in small amounts. The resulting suspension was allowed to stand at room temperature for 30 minutes and then a solution of 4.5 g of the said aldehyde in 50 ml of dimethoxyethane was added thereto. The reaction mixture was heated to 60° C. and 10 ml of dimethylsulfoxide were added thereto. The mixture was held at 60° C. for 90 minutes and was evaporated to dryness. The residue was taken up in aqueous monosodium phosphate solution and the mixture was extracted with ether. The ether phase was dried over magnesium sulfate and was evaporated to dryness. The residue was chromatographed over silica gel and was eluted with an 8-2 ethyl acetate-cyclohexane mixture to obtain 2.5 g of methyl (5RS,(1′E) 2-methoxy-5-[3′-oxo-4′-(3″-thienyloxy)-1′-butenyl]-1-cyclopentene-carboxylate with an Rf=0.4.

NMR Spectrum (CDCl₃, 60 MHz):

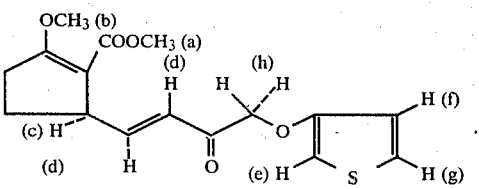

(a): 3.66 p.p.m.
(b): 3.89 p.p.m.
(c): 3.5 to 3.92 p.p.m.
(d): 6.4 p.p.m. (doublet J:16 MHz); 6.95 p.p.m.–7.2 p.p.m. (2 doublets J:8 Hz)

(e): 6.25 p.p.m.
(f): 6.82 p.p.m.–6.9 p.p.m. (2 doublets J:2 Hz)
(g): 7.24 p.p.m.–7.32 p.p.m. (2 doublets J:3 Hz)
(h): 4.69 p.p.m.

STEP B: Methyl (5Rs, 3'SR)(1'E) 2-methoxy-5-[3'-hydroxy-4'-(3''-thienyloxy)-1'-butenyl]-1-cyclopentene-carboxylate and methyl (5RS, 3'RS)(1'E) 2-methoxy-5-[3'-hydroxy-4'-(3''-thienyloxy)-1'-butenyl]-1-cyclopentene-carboxylate 418 mg of potassium borohydride were added with stirring to a solution of 2.5 g of the product of Step A in 50 ml of a 4-1 methanol-water mixture and after stirring the suspension for 2 hours at room temperature, 20 ml of an aqueous saturated monosodium phosphate solution were added thereto. The mixture was evaporated to dryness under reduced pressure and the residue was extracted with ethyl acetate. The organic extracts were dried and evaporated to dryness under reduced pressure and the residue was chromatographed over silica gel. Elution with a 4-1 methylene chloride-ethyl acetate mixture yielded 0.82 g of methyl (5RS, 3'RS)(1'E) 2-methoxy-5-[3'-hydroxy-4'-(3''-thienyloxy)-1'-butenyl]-1-cyclopentene-carboxylate with an Rf=0.22 and 0.88 g of methyl (5RS, 3'SR)(1'E) 2-methoxy-5-[3'-hydroxy-4'-(3''-thienyloxy)-1'-butenyl]-cyclopentene-carboxylate with an Rf=0.24.

IR Spectrum (CHCl$_3$):

Both isomers had the same IR spectrum: OH at 3579 cm$^{-1}$; conjugated ester

at 1695 cm$^{-1}$ and conjugated —C=C— at 1627 cm$^{-1}$

NMR Spectrum (CDCl$_3$-60 MHz):

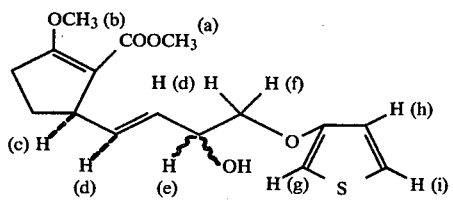

(a): 3.7 p.p.m.
(b): 3.87 p.p.m.
(c): 3.66 p.p.m.
(d): 5.33 to 6.0 p.p.m.
(e): 4.58 p.p.m.
(f): 3.92 p.p.m. (doublet J=6 Hz)
(g): 6.33 p.p.m.
(h): 6.83 p.p.m.
(i): 7.25 p.p.m.

STEP C: Methyl (1RS, 5RS, 3'RS)(1'E) 2-oxo-5-[3'-hydroxy-4'-(3''-thienyloxy)-1'-butenyl]-cyclopentane-carboxylate 820 mg of the (3'RS) isomer of Step B were dissolved with stirring in 60 ml of a 1-2 methanol-water mixture and 900 mg of oxalic acid were added thereto. The mixture was stirred at room temperature for 5 hours and was evaporated to dryness under reduced pressure. The residue was extracted with chloroform and the organic phase was dried and evaporated to dryness under reduced pressure. The residue was chromatographed over silica gel and was eluted with a 2-3 cyclohexane-ethyl acetate mixture to obtain 0.6 g of methyl (1RS, 5RS, 3'RS)(1'E) 2-oxo-5-[3'-hydroxy-4'-(3''-thienyloxy)-1'-butenyl]-cyclopentane-carboxylate with a Rf=0.35.

IR Spectrum (CHCl$_3$):

C=O at 1802 cm$^{-1}$ (shoulder), at 1757 and 1732 cm$^{-1}$; thienyloxy at 1543 cm$^{-1}$ and associated OH at 3567 cm$^{-1}$.

NMR Spectrum (CDCl$_3$-60 MHz):

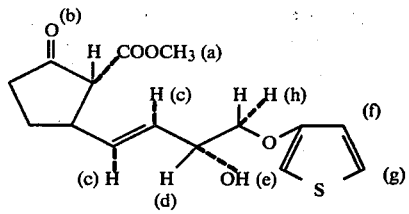

(a): 3.74 p.p.m.
(b): 2.99 p.p.m. (double J: 11 Hz)
(c): 5.5 to 6 p.p.m.
(d): 4.38 to 4.63 p.p.m.
(e): 6.25 p.p.m.
(f): 6.76 p.p.m.
(g): 7.16 p.p.m.
(h): 3.67 mto 4 p.p.m.

STEP D: Methyl (1RS, 2SR, 5RS, 3'RS)(1'E) 2-hydroxy-5-[3'-hydroxy-4'-(3''-thienyloxy)-1'-butenyl]-cyclopentane-carboxylate A solution of 0.6 g of the product of Step C in 15 ml of tetrahydrofuran cooled to −60° C. was added over 10 minutes at −60° C. to 6.75 ml of a solution of molar L-selectride in tetrahydrofuran and the reaction mixture was stirred at −60° C. for one hour and was then poured into an aqueous saturated monosodium phosphate solution. The mixture was extracted with ethyl acetate and the organic extracts were dried over magnesium sulfate and evaporated to dryness under reduced pressure. The residue was chromatographed over silica gel and was eluted with a 4-6 cyclohexane-ethyl acetate mixture to obtain 530 mg of methyl (1RS, 2SR, 5RS, 3'RS)(1'E) 2-hydroxy-5-[3'-hydroxy-4'-(3''-thienyloxy)-1'-butenyl]-cyclopentane-carboxylate with an Rf=0.2.

IR Spectrum (CHCl$_3$):

C=O towards 1732-1739 cm$^{-1}$ and an important shoulder at 1715 cm$^{-1}$

NMR Spectrum (CDCl$_3$-90 MHz):

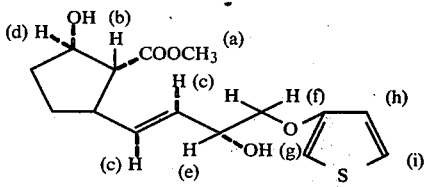

(a): 3.72 p.p.m.
(b): 2.43 p.p.m.–2.48 p.p.m. (2 doublets J: 5 Hz)
(c): 5.46 to 6.05 p.p.m.
(d): 4.41 to 4.58 p.p.m.
(e): 4.41 to 4.58 p.p.m.
(f): 3.62 to 4.08 p.p.m.

(g): 6.27 to 6.34 p.p.m.
(h): 6.75 to 6.84 p.p.m.
(i): 7.14 to 7.25 p.p.m.

STEP E: (1RS, 2SR, 5RS, 3'RS)(1'E) 2-hydroxy-5-[3'-hydroxy-4'-(3''-thienyloxy)-1'-butenyl]-cyclopentane carboxylic acid 4.89 ml of 1 N sodium hydroxide solution were added all at once to a mixture of 0.51 g of the product of Step D, 15 ml of water and 10 ml of methanol and the reaction mixture was stirred at room temperature for 3 hours and was then evaporated to dryness under reduced pressure. 20 ml of water were added to the residue and the mixture was extracted with ether. The aqueous phase was acidified with 1 N hydrochloric acid and was then extracted with ethyl acetate. The organic extracts were dried and evaporated to dryness to obtain 400 mg of (1RS, 2SR, 5RS, 3'RS)(1'E) 2-hydroxy-5-[3'-hydroxy-4'-(3''-thienyloxy)-1'-butenyl]-cyclopentane carboxylic acid which was used as is for the next step.

STEP F: Lactone of (1RS, 2SR, 5RS, 3'RS)(1'E) 2-hydroxy-5-[3'-hydroxy-4-(3''-thienyloxy)-1'-butenyl]-cyclopentane-1-carboxylic acid A mixture of 600 mg of the product of Step E, 15 ml of chloroform and 267 mg of tosyl chloride was stirred until dissolution and then 1.2 g of diazabicyclooctane was added thereto. The mixture was stirred at room temperature for one hour and was filtered. The filtrate was washed with 1 N hydrochloric acid and the acid solution was extracted with ethyl acetate. The organic extracts were dried and evaporated to dryness under reduced pressure. The residue was chromatographed over silica gel and was eluted with a 1-1 cyclohexaneethyl acetate mixture to obtain 130 mg of lactone (1RS, 2SR, 5RS, 3'RS)(1'E) 2-hydroxy-5-[3'-hydroxy-4-(3''-thienyloxy)-1'-butenyl]-cyclopentane-1-carboxylic acid with an Rf=0.4

IR Spectrum (CHCl$_3$):

OH at 3579 cm$^{-1}$; lactone at 1827 cm$^{-1}$; C=C at 1672-969 cm$^{-1}$ and conjugated thienyloxy system at 1546 cm$^{-1}$.

NMR Spectrum (CDCl$_3$-90 MHz):

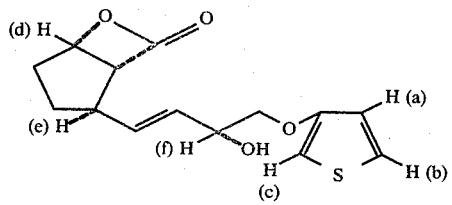

(a): 6.75 to 6.85 p.p.m.
(b): 7.20 to 7.26 p.p.m.
(c): 6.30 to 6.35 p.p.m.
(d): 5.05 p.p.m. (triplet J: 4 hz)
(e): 3.15 p.p.m. (triplet J: 6 hz)
(f): 4.41 to 4.60 p.p.m.

EXAMPLE 2

Lactone of (1RS, 2SR, 5RS, 3'SR)(1'E) 2-hydroxy-5-[3'-hydroxy-4'-(3''-thienyloxy)-1'-butenyl]-cyclopropane-1-carboxylic acid STEP A: Methyl (1RS, 5RS, 3'SR)(1'E) 2-oxo-5-[3'-hydroxy-4-(3''-thienyloxy)-1'-butenyl]-cyclopropane-1-carboxylate A mixture of 880 mg of the (3'SR) isomer of Step B of Example 1, 40 ml of water, 20 ml of methanol and 900 mg of oxalic acid was stirred at room temperature for 5 hours and the mixture was evaporated to dryness under reduced pressure. The residue was extracted with chloroform and the organic extracts were dried and evaporated to dryness under reduced pressure. The residue was chromatographed over silica gel and was eluted with an 8-2 methylene chloride-ethyl acetate mixture to obtain 730 mg of methyl (1RS, 5RS, 3'SR)(1'E) 2-oxo-5-[3'-hydroxy-4-(3''-thienyloxy)-1'-butenyl]-cyclopropane-1-carboxylate with an RF=0.35. The product had the same constants as its diastereoisomer of Step C of Example 1.

STEP B: Methyl (1RS, 2SR, 5RS, 3'SR)(1'E) 2-hydroxy-5-[3'-hydroxy-4'-(3''-thienyloxy)-1'-butenyl]-cyclopentane-carboxylate A solution of 0.365 g of the product of Step A in 10 ml of tetrahydrofuran was added over 10 minutes at −60° C. to 4.1 ml of a molar solution of L-selectride in tetrahydrofuran and the mixture was stirred at −60° C. for one hour and was then poured into an aqueous saturated monosodium phosphate solution. The mixture was extracted with ethyl acetate and the organic extracts were dried and evaporated to dryness under reduced pressure. The residue was chromatographed over silica gel and was eluted with a 4-6 cyclohexaneethyl acetate mixture to obtain 230 mg of methyl (1RS, 2SR, 5RS, 3'SR)(1'E) 2-hydroxy-5-(3'-hydroxy-4'-(3''-thienyloxy)-1'-butenyl]-cyclopentane-carboxylic with an Rf=0.2. Its constants were the same as its diastereoisomer of Step D of Example 1.

STEP C: (1RS, 2SR, 5RS, 3'SR)(1'E) 2-hydroxy-5-[3'-hydroxy-4'-(3''-thienyloxy)-1'-butenyl]-cyclopentane-carboxylic acid A mixture of 0.23 g of the product of Step B, 10 ml of water and 6 ml of methanol was stirred while 2.2 ml of 1 N sodium hydroxide solution was added thereto all at once and the mixture was stirred at room temperature for 3 hours and was evaporated to dryness. 20 ml of water were added to the residue and the mixture was washed 3 times with ether and was acidified with 1 N hydrochloric acid. The aqueous phase was extracted with ethyl acetate and the organic phase was dried and evaporated to dryness to obtain 400 mg of (1RS, 2SR, 5RS, 3'SR)(1'E) 2-hydroxy-5-[3'-hydroxy-4'-(3''-thienyloxy)-1'-butenyl]-cyclopentane-carboxylic acid.

STEP D: Lactone of (1RS, 2SR, 5RS, 3'SR)(1'E) 2-hydroxy-5-[3'-hydroxy-4'-(3''-thienyloxy)-1'-butenyl]-cyclopentane-1-carboxylic acid A mixture of 197 mg of the product of Step C, 10 ml of chloroform and 131.7 mg of tosyl chloride was stirred until dissolution occured and 0.592 g of diazabicyclooctane was added thereto. The mixture was stirred at room temperature for one hour and was vacuum filtered. The filtrate was washed with 1 N hydrochloric acid and the acid solution was extracted with ether. The combined ether phases were dried and evaporated to dryness under reduced pressure. The residue was chromatographed over silica gel and was eluted with a 7-3 methylene chloride-ethyl acetate mixture to obtain 100 mg of lactone of (1RS, 2SR, 5RS, 3′SR)(1′E) 2-hydroxy-5-[3′-hydroxy-4′-(3″-thienyloxy)-1′-butenyl]-cyclopentane-1-carboxylic acid with an Rf=0.45.

IR Spectrum (CHCl₃):

OH at 3579 cm⁻¹; β-lactam at 1827 cm⁻¹; C═C at 1672–969 cm⁻¹; conjugated thienyloxy system at 1546 cm⁻¹.

NMR Spectrum (CDCl₃-90 MHz):

(a): 6.75 to 6.85 p.p.m.
(b): 7.20 to 7.26 p.p.m.
(c): 6.30 to 6.35 p.p.m.
(d): 5.05 p.p.m.
(e): 3.15 p.p.m.
(f): 5.4 to 5.92 p.p.m.
(g): 4.4 to 4.6 p.p.m.

EXAMPLE 3

Lactone of (1RS, 2SR, 5SR, 3′RS-SR)(1′E) 2-hydroxy-5-[3′-hydroxy-4′,4′-dimethyl-6′-oxa-1′-octenyl]-cyclopentane carboxylic acid STEP A: Methyl (1RS, 2SR, 5SR) 2-hydroxy-5-(α-tetrahydropyranyloxy)-methyl-cyclopentane-carboxylate A solution of 7 g of methyl (1RS, 5SR) 2-oxo-5-(α-tetrahydropyranyloxy)-methyl-cyclopentane-carboxylate in 50 ml of tetrahydrofuran was added dropwise with stirring to 100 ml of L-selectride cooled to −70° C. and the mixture was stirred at −70° C. for 90 minutes. The mixture was poured into an iced aqueous saturated monosodium phosphate solution and the mixture was extracted with ethyl acetate. The extracts were dried and evaporated to dryness and the residue was chromatographed over silica gel. Elution with a 1—1 cyclohexane-ethyl acetate miture yielded 3.925 g of methyl (1RS, 2SR, 5SR) 2-hydroxy-5-(α-tetrahydropyranyloxy)-methyl cyclopentane-carboxylate with an Rf=0.18.

IR Spectrum (CHCl₃):
C═O at 1739–1715 cm⁻¹
NMR Spectrum (CDCl₃-60 MHz):

(a): 2.67 p.p.m.
(b): 4.45 p.p.m.
(c): 3.17 to 4.17 p.p.m.
(d): 4.6 p.p.m.
(f): 3.74 p.p.m.–3.66 p.p.m.

STEP B: (1RS, 2SR, 5SR) 2-hydroxy-5-(α-tetrahydropyranyloxy)-methylcyclopentane carboxylic acid 15.1 ml of 2 N sodium hydroxide solution were added under an inert atmosphere to a solution of 3.9 g of the product of Step A in 40 ml of methanol and the mixture was stirred at room temperature for 6 hours. The mixture was poured into water and the mixture was acidified with monosodium phosphate. The mixture was extracted with ethyl acetate. The extracts were dried and evaporated to dryness to obtain 3.626 g of (1RS, 2SR, 5SR) 2-hydroxy-5-(α-tetrahydropyranyloxy)-methylcyclopentane carboxylic acid.

IR Spectrum (CHCl₃):
COOH at 1737 cm⁻¹

STEP C: Lactone of (1RS, 2SR, 5SR) 2-hydroxy-5-(α-tetrahydropyranyloxy)-methylcyclopentane carboxylic acid 6.43 g of diazabicyclooctane and 3.277 g of tosyl chloride were added to a solution of 3.5 g of (1RS, 2SR, 5SR) 2-hydroxy-5-(α-tetrahydropyranyloxy)-methylcyclopentane carboxylic acid in 70 ml of chloroform and the resulting solution was stirred under an inert atmosphere for 2½ hours and was then poured in an aqueous saturated monosodium phosphate solution. The mixture was extracted with chloroform and the organic phase was washed with water, dried and evaporated to dryness. The residue was chromatographed over silica gel and was eluted with a 6–4 cyclohexane-ethyl acetate mixture to obtain 1.694 g of lactone of (1RS, 2SR, 5SR) 2-hydroxy-5-(α-tetrahydropyranyloxy)-methylcyclopentane carboxylic acid.

IR Spectrum (CHCl₃):
C═O at 1818 cm⁻¹ complex
RMN Spectrum (CDCl₃-60 MHz):

(a): 3.88 p.p.m. (triplet J=3 Hz)
(b): 5.02 p.p.m. (triplet J=3 Hz)
(c) (e) 3 to 4.p.p.m.
(d): 4.55 p.p.m.

STEP D: Lactone of (1RS, 2SR, 5SR) 2-hydroxy-5-hydroxymethylcyclopentane-carboxylic acid 555 mg of oxalic acid were added to a solution of 1.66 g of the product of Step C, 32 ml of ethanol and 3.2 ml of water and the reaction mixture was heated under an inert atmosphere for 4½ hours and was evaporated to dryness. The residue was taken up in water and the aqueous phase was extracted with chloroform. The organic phase was dried and evaporated to dryness under reduced pressure. The residue was chromatographed over silica gel and was eluted with a 4-6 cyclohexane-ethyl acetate mixture to obtain 542 mg of lactone of (1RS, 2SR, 5SR) 2-hydroxy-5-hydroxymethyl-cyclopentanecarboxylic acid with an Rf=0.14.

IR Spectrum (CHCl₃):
Presence of OH and β-lactam
NMR Spectrum (CDCl₃-60 MHz):

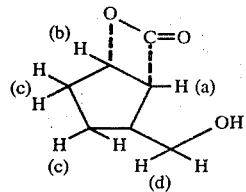

(a): 3.90 p.p.m. (doublet J: 3.5 Hz)
(b): 5.03 p.p.m. (triplet J: 3.5 Hz)
(c): 1.5 to 2.83 p.p.m.
(d): 3.45 p.p.m.

STEP E: Lactone of (1RS, 2SR, 5RS)(1'E) 2-hydroxy-5-(3'-oxo-4',4'-dimethyl-6'-oxa-1'-octenyl)-cyclopentane-carboxylic acid 3.4 ml of pyridine and 2.11 g of chromic acid anhydride were added in small fractions with stirring to 60 ml of methylene chloride and the mixture was stirred for 30 minutes at room temperature. A solution of 500 mg of the product of Step D in 2 ml of methylene chloride was added thereto and the mixture was stirred at room temperature for 30 minutes and was filtered. The filtrate was evaporated to dryness to obtain 1.070 g of aldehyde.

A solution of 1.064 g of dimethyl 2-oxo-3,3-dimethyl-5-oxa-heptanyl-phosphonate in 12 ml of dimethoxyethane was added with stirring to a suspension of 202 mg of sodium hydride in 50% oil suspension and 12 ml of dimethoxyethane. The mixture was stirred for one hour at room temperature and after cooling the solution to −35° C., a solution of 1.070 g of said aldehyde in 12 ml of dimethoxyethane was added thereto over 20 minutes. The mixture was stirred for 30 minutes and was then poured into an aqueous saturated monosodium phosphate solution. The mixture was extracted with ethyl acetate and the organic phase was dried over magnesium sulfate and evaporated to dryness. The residue was chromatographed over silica gel and was eluted with a 7-3 cyclohexaneethyl acetate mixture to obtain 394 mg of lactone of (1RS, 2SR, 5RS)(1'E) 2-hydroxy-5-(3'-oxo-4',4'-dimethyl-6'-oxa-1'-octenyl)-cyclopentane-carboxylic acid with an Rf=0.4.

IR Spectrum (CHCl₃):
lactone at 1828 cm⁻¹; shoulder at 1810 cm⁻¹; conjugated ketone at 1693–1626 cm⁻¹.
NMR Spectrum (CDCl₃-60 MHz)

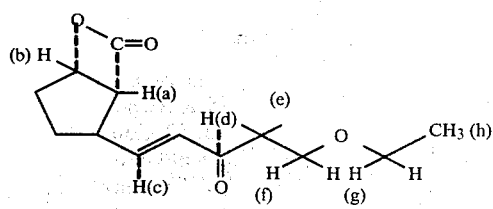

(a): 3.84 p.p.m. (doublet J=5 Hz)
(b): 5.05 p.p.m. (triplet J=3 Hz)
(c): 6.77 p.p.m. (doublet J=5 Hz)
(d): 6.42 p.p.m. (doublet J=4 Hz)
(e): 1.13 p.p.m.
(f): 3.42 p.p.m.
(g): 3.46 p.p.m. (quadruplet J: 7 Hz)
(h): 1.13 p.p.m. (triplet J: 7 Hz)

STEP F: Lactone [1R, 2SR, 5RS, 3'(SR-RS)](1'E) 2-hydroxy-5-(3'-hydroxy-4',4'-dimethyl-6'-oxa-1'-octenyl)-cyclopentane carboxylic acid 2.9 ml of a 0.4 molar zinc borohydride solution were added dropwise at 0° C. to a solution of 392 mg of the product of Step E in 21.5 ml of dimethoxyethane and after the temperature returned to room temperature, the mixture was stirred for 2 hours and then was poured into an aqueous saturated monosodium phosphate solution. The mixture was extracted with ethyl acetate and the organic phase was dried and evaporated to dryness. The residue was chromatographed over silica gel and was eluted with a 6-4 cyclohexane-ethyl acetate mixture to obtain 251 mg of lactone of [1RS, 2SR, 5RS, 3'(SR-RS)](1'E) 2-hydroxy-5-(3'-hydroxy-4',4'-dimethyl-6'-oxa-1'-octenyl)-cyclopentane carboxylic acid with an Rf=0.26.

IR Spectrum (CHCl₃):
C═O at 1822 cm⁻¹; shoulder at 1806 cm⁻¹; C═C at 1668 cm⁻¹ and 973 cm⁻¹; free OH at 3610 cm⁻¹; associated OH at 3448 cm⁻¹
NMR Spectrum (CDCl₃-60 MHz):

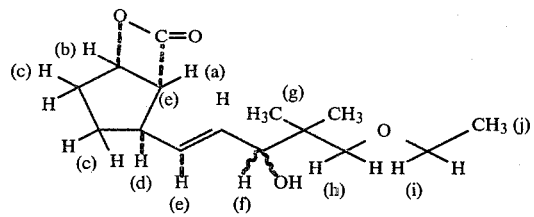

(a) (f): 3.83 p.p.m.
(b): 5.05 p.p.m. (triplet J: 3 Hz)
(c): 1.5 to 2.33 p.p.m.
(d): 3.17 p.p.m.
(e): 5.53 p.p.m.
(g): 0.87 p.p.m.
(h): 3.28 p.p.m.
(i): 3.47 p.p.m. (quadruplet J: 7 Hz)
(j): 1.18 p.p.m. (triplet J: 7 Hz)

EXAMPLE 4

Lactone of (1RS, 2SR, 5RS, 3'RS)(1'E) 2-hydroxy-5-[3'-hydroxy-4'-phenoxy-1'-butenyl]-cyclopentane-1-carboxylic acid STEP A: Methyl (5RS)(1'E) 2-methoxy-5-[3'-oxo-4'-phenoxy-1'-butenyl]-1-cyclopentene-carboxylate 65 mg of sodium hydride as a 60% mineral oil suspension were slowly added under an inert atmosphere with stirring to 5 ml of dimethoxy-ethane and a solution of 413 mg of dimethyl 2-oxo-3-(3'-phenoxy)-propyl phosphate in 5 ml of dimethoxyethane were added thereto. The mixture was stirred for 2 hours at 20° C. and a solution of 290 mg of methyl (RS) 2-methoxy-5-formyl-1-cyclopentene-carboxylate in 5 ml of dimethoxyethane was added to the suspension. The mixture was stirred at 20° C. for 24 hours and was then poured into an iced aqueous saturated monosodium phosphate solution. The mixture was extracted with ethyl acetate and the organic phase was washed with water, dried and evaporated to dryness. The residue was chromatographed over silica gel and was eluted with a 1-1 cyclohexane-ethyl acetate mixture containing 0.2% of triethylamine to obtain 174 mg of methyl (5RS)(1'E) 2-methoxy-5-[3'-oxo-4'-phenoxy-1'-butenyl]-1-cyclopentene-carboxylate which after crystallization from an isopropyl ether-ether mixture melted at 90° C.

STEP B: Methyl (5RS, 3'RS)(1'E) 2-methoxy-5-[3'-hydroxy-4'-phenoxy-1'-butenyl]-1-cyclopentene-carboxylate and methyl (5RS, 3'SR)(1'E) 2-methoxy-5-[3'-hydroxy-4'-phenoxy-1'-butenyl]-1-cyclopentene-carboxylate Using the procedure of Step B of Example 1, 392 mg of the product of Step B were reacted and the residue was chromatographed over silica gel. Elution with a 9-1 methylene chloride-ethyl acetate mixture containing 0.1% of triethylamine yielded 110 mg of methyl (5RS,3'RS)(1'E) 2-methoxy-5-[3'-hydroxy-4'-phenoxy-1'-butenyl]-1-cyclopentene-carboxylate with an Rf=0.35 and 130 mg of methyl (5RS, 3'SR) (1'E) 2-methoxy-5-[3'-hydroxy-4'-phenoxy-1'-butenyl]-1-cyclopentene-carboxylate with an Rf=0.40.

STEP C: Methyl (1RS, 5RS, 3'RS)(1'E) 2-oxo-5-[3'-hydroxy-4'-phenoxy-1'-butenyl]-cyclopentane carboxylate Using the procedure of Step C of Example 1, 110 mg of the (3'RS) isomer of Step B were reacted and the residue was chromatographed over silica gel. Elution with an 85-15 methylene chloride-ethyl acetate mixture yielded 84 mg of methyl (1RS, 5RS, 3'RS)(1'E) 2-oxo-5-[3'-hydroxy-4'-phenoxy-1'-butenyl]-cyclopentane carboxylate with an Rf=0.35.

STEP D: Methyl (1RS, 2SR, 5RS, 3'RS)(1'E) 2-hydroxy-5-[3'-hydroxy-4'-phenoxy-1'-butenyl]-cyclopentane-carboxylate Using the procedure of Step D of Example 1, 116 mg of the product of Step C were reacted and the residue was chromatographed over silica gel. Elution with an 85-15 methylene chloride-ethyl acetate mixture yielded 85 mg of methyl (1RS, 2SR, 5RS, 3'RS)(1'E) 2-hydroxy-5-[3'-hydroxy-4'-phenoxy-1'-butenyl]-cyclopentane-carboxylate with an Rf=0.13 and which melted at 109° C. after crystallization from an ether-isopropyl ether mixture.

STEP E: (1RS, 2SR, 5RS, 3'RS)(1'E) 2-hydroxy-5-[3'-hydroxy-4'-phenoxy-1'-butenyl]-cyclopentane carboxylic acid Using the procedure of Step E of Example 1, 85 mg of the product of Step D were reacted to obtain 71 mg of (1RS, 2SR, 5RS, 3'RS)(1'E) 2-hydroxy-5-[3'-hydroxy-4'-phenoxy-1'-butenyl]-cyclopentane carboxylic acid melting at 146° C.

STEP F: Lactone of (1RS, 2SR, 5RS, 3'RS)(1'E) 2-hydroxy-5-[3'-hydroxy-4'-phenoxy-1'-butenyl]-cyclopentane-1-carboxylic acid Using the procedure of Step F of Example 1, 71 mg of the product of Step E were reacted and the residue was chromatographed over silica gel. Elution with a 95-5 methylene chloride-ethyl acetate mixture yielded 42 mg of lactone of (1RS, 2SR, 5RS, 3'RS)(1'E) 2-hydroxy-5-[3'-hydroxy-4'-phenoxy-1'-butenyl]-cyclopentane-1-carboxylic acid with an Rf=0.25 and a melting point of 83° C.

IR Spectrum (CHCl3):
OH at 3580 cm$^{-1}$; lactone at 1821 cm$^{-1}$; C=C at 968 cm$^{-1}$; aromatic bonds at 1598-1586-1495 cm$^{-1}$ NMR Spectrum (CDCl3-90 MHz):

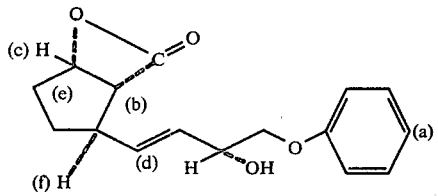

(a): 4.53 to 4.96 p.p.m.
(b): 3.53 to 3.99 p.p.m.
(c): 3.31–3.35 and 3.39 p.p.m.
(d): 2.99 p.p.m. (multiplet)
(e): 2.43 to 2.74 p.p.m.
(f): 2.09 p.p.m.

EXAMPLE 5

Lactone of (1RS, 2SR, 5RS, 3'SR)(1'E) 2-hydroxy-5-[3'-hydroxy-4'-phenoxy-1'-butenyl]-cyclopentane-1-carboxylic acid STEP A: Methyl (1RS, 5RS, 3'SR)(1'E) 2-oxo-5-[3'-hydroxy-4'-phenoxy-1'-butenyl]-cyclopentane-carboxylate Using the procedure of Step A of Example 2, the (3'SR) of Step B of Example 4 was reacted and the residue was chromatographed over silica gel. Elution with an 8-2 methylene chloride-ethyl acetate mixture yielded methyl (1RS, 5RS, 3'SR)(1'E) 2-oxo-5-[3'-hydroxy-4'-phenoxy-1'-butenyl]-cyclopentane-carboxylate with an Rf=0.35.

STEP B: Methyl (1RS, 2SR, 5RS, 3'SR)(1'E) 2-hydroxy-5-[3'-hydroxy-4'-phenoxy-1'-butenyl]-cyclopentane-carboxylate Using the procedure of Step B of Example 2, the product of Step A was reacted and the residue was chromatographed over silica gel. Elution with a 4-6 cyclohexane-ethyl acetate mixture yielded (1RS, 2SR, 5RS, 3'SR)(1'E) 2-hydroxy-5'[3'-hydroxy-4'-phenoxy-1'-butenyl]-cyclopentane-carboxylate with an Rf=0.2.

STEP C: (1RS, 2SR, 5RS, 3'SR)(1'E) 2-hydroxy-5-[3'-hydroxy-4'-phenoxy-1'-butenyl]-cyclopentane-carboxylic acid Using the procedure of Step C of Example 2, the product of Step B was reacted to obtain (1RS, 2SR, 5RS, 3'SR) (1'E) 2-hydroxy-5-[3'-hydroxy-4'-phenoxy-1'-butenyl]-cyclopentane-carboxylic acid.

STEP D: Lactone of (1RS, 2SR, 5RS, 3'SR)(1'E) 2-hydroxy-5-[3'-hydroxy-4'-phenoxy-1'-butenyl]-cyclopentane-1-carboxylic acid Using the procedure of Step D of Example 2, the product of Step C was reacted and the residue was chromatographed over silica gel. Elution with a 95-5 methylene chloride-ethyl acetate mixture yielded lactone of (1RS, 2SR, 5RS, 3'SR)(1'E) 2-hydroxy-5-[3'-hydroxy-4'-phenoxy-1'-butenyl]-cyclopentane-1-carboxylic acid with an Rf=0.25 and a melting point of 90° C.

EXAMPLE 6

Gelules were prepared containing 1 mg or 5 mg of the product of Example 1 and sufficient excipient for a final weight of 400 mg. Injectable solutions were also prepared with 1 mg or 5 mg of the product of Example 2 and sufficient sterile water for a final volume of 5 ml.

PHARMACOLOGICAL DATA

A. Hypotensive activity in rabbits

The products were administered as a solution in physiological serum containing 10% of ethanol intraveinously to rabbits anesthetized with urethane. The carotidine pressure was measured and the dose which lowered the pressure by 30% was 50 μg/kg for the product of example 1, <30 μg/kg for the product of example 2, <20 μg/kg for the product of example 4 and 10 μg/kg for the product of example 5.

B. Hypotensive activity in Dogs

Adult bastard dogs of both sexes weighing 14 to 20 kg with a closed thorax were anesthetized with a barbiturate mixture. The traechas was intubed and the animals were artificially ventilated with a pump. The arterial pressure of the carotide was ascertained with a pressure head and the dose which reduced the arterial pressure by 20% for at least 20 minutes was determined to be 1 mg/kg for the product of Example 2.

Various modifications of the products and processes of the invention may be made without departing from the spirit or scope thereof and it is to be understood that the invention is to be limited only as defined in the appended claims.

We claim:

1. A β-lactone of 2-hydroxy-cyclopentane-carboxylic acid of the formula

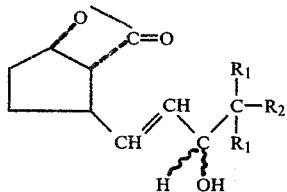

wherein $R_1$ is selected from the group consisting of hydrogen and methyl and $R_2$ is selected from the group consisting of $-CH_2-O-CH_2-CH_3$ and $-X-Ar$, X is selected from the group consisting of $-O-$ and $-CH_2-$, Ar is an optionally substituted member selected from the group consisting of thienyl, thiazolyl, phenyl and thiadiazolyl, the optional substituents being at least one member selected from the group consisting of halogen and $-CF_3$ and the wavy line indicates that the groups may be in the α,β or β,α-positions or mixtures thereof.

2. A compound of claim 1 wherein $R_2$ is selected from the group consisting of thien-3-yloxy, thiazol-2-yloxy, 1,2,5-thiadiazol-3-yloxy, phenoxy and ethoxymethyl.

3. A compound of claim 1 which is the lactone of (1RS, 2SR, 5RS, 3'SR)(1'E) 2-hydroxy-5-[3'-hydroxy-4'-(3''-thienyloxy)-1'-butenyl]-cyclopentane-1-carboxylic acid.

4. A compound of claim 1 which is the lactone of (1RS, 2SR, 5RS, 3'RS)(1'E) 2-hydroxy-5-[3'-hydroxy-4'-(3''-thienyloxy)-1'-butenyl]-cyclopentane-1-carboxylic acid.

5. A compound of claim 1 which is the lactone of (1RS, 2SR, 5RS, 3'RS)(1'E) 2-hydroxy-5-[3'-hydroxy-4'-phenoxy-1'-butenyl]-cyclopentane-1-carboxylic acid.

6. A compound of claim 1 which is the lactone of (1RS, 2SR, 5RS, 3'SR)(1'E) 2-hydroxy-5-[3'-hydroxy-4'-phenoxy-1'-butenyl]-cyclopentane-1-carboxylic acid.

7. A compound of claim 1 which is the lactone of (1RS, 2SR, 5RS, 3'RS-3'SR)(1'E) 2-hydroxy-5-[3'-hydroxy-4',4'-dimethyl-6-oxa-1'-octenyl]-cyclopentanecarboxylic acid.

8. A hypotensive composition comprising a hypotensively effective amount of a compound of claim 1 and an inert pharmaceutical carrier.

9. A composition of claim 8 wherein $R_2$ is selected from the group consisting of thien-3-yloxy, thiazol-2-yloxy, 1,2,5-thiadiazol-3-yloxy, phenoxy and ethoxymethyl.

10. A composition of claim 8 which is the lactone of (1RS, 2SR, 5RS, 3'SR)(1'E) 2-hydroxy-5-[3'-hydroxy-4'-(3''-thienyloxy)-1'-butenyl]-cyclopentane-1-carboxylic acid.

11. A composition of claim 8 which is the lactone of (1RS, 2SR, 5RS, 3'RS)(1'E) 2-hydroxy-5-[3'-hydroxy-4'-(3''-thienyloxy)-1'-butenyl]-cyclopentane-1-carboxylic acid.

12. A composition of claim 8 which is the lactone of (1RS, 2SR, 5RS, 3'RS)(1'E) 2-hydroxy-5-[3'-hydroxy-4'-phenoxy-1'-butenyl]-cyclopentane-1-carboxylic acid.

13. A composition of claim 8 which is the lactone of (1RS, 2SR, 5RS, 3'SR)(1'E) 2-hydroxy-5-[3'-hydroxy-4'-phenoxy-1'-butenyl]-cyclopentane-1-carboxylic acid.

14. A composition of claim 8 which is the lactone of (1RS, 2SR, 5RS, 3'RS-3'SR)(1'E) 2-hydroxy-5-[3'-hydroxy-4',4'-dimethyl-6-oxa-1'-octenyl]-cyclopentane-1-carboxylic acid.

15. A method of lowering blood pressure in warm-blooded animals comprising administering to warm-blooded animals a hypotensively effective amount of a compound of claim 1.

16. A method of claim 15 wherein $R_2$ is selected from the group consisting of thien-3-yloxy, thiazol-2-yloxy, 1,2,5-thiadiazol-3-yloxy, phenoxy and ethoxymethyl.

17. A method of claim 15 wherein the compound is the lactone of (1RS, 2SR, 5RS, 3'SR)(1'E) 2-hydroxy-5-[3'-hydroxy-4'-(3''-thienyloxy)-1'-butenyl]-cyclopentane-1-carboxylic acid.

18. A method of claim 15 wherein the compound is the lactone of (1RS, 2SR, 5RS, 3'RS)(1'E) 2-hydroxy-5-[3'-hydroxy-4'-(3''-thienyloxy)-1'-butenyl]-cyclopentane-1-carboxylic acid.

19. A method of claim 15 wherein the compound is the lactone of (1RS, 2SR, 5RS, 3'RS)(1'E) 2-hydroxy-5-[3'-hydroxy-4'-phenoxy-1'-butenyl]-cyclopentane-1-carboxylic acid.

20. A method of claim 15 wherein the compound is the lactone of (1RS, 2SR, 5RS, 3'SR)(1'E) 2-hydroxy-5-[3'-hydroxy-4'-phenoxy-1'-butenyl]-cyclopentane-1-carboxylic acid.

21. A method of claim 15 wherein the compound is the lactone of (1RS, 2SR, 5RS, 3'RS-3'SR)(1'E) 2-hydroxy-5-[3'-hydroxy-4',4'-dimethyl-6-oxa-1'-octenyl]-cyclopentane-carboxylic acid.

* * * * *

UNITED STATES PATENT AND TRADEMARK OFFICE
CERTIFICATE OF CORRECTION

PATENT NO. : 4,264,623
DATED : April 28, 1981
INVENTOR(S) : JEAN BUENDIA ET AL.

It is certified that error appears in the above—identified patent and that said Letters Patent is hereby corrected as shown below:

Abstract, 4th line from bottom: "thw" should read -- the --.

Column 1, line 55; Column 18, line 18: "ethox-" should read -- ethoxy- --.

Column 1, line 56; column 6, line 29; column 18, line 19: "ymethyl" should read -- methyl --.

Column 3, line 52: "trismethox-" should read -- trismethoxy- --.

line 53: "yborohydride" should read -- borohydride --.

Column 5, line 48: After "arabic" delete the comma ",".

Column 6, line 28: "hydrox-" should read -- hydroxy- --.

Column 7, line 26: Before "-cyclopentene" insert -- -1 --.

Column 7: The portion of the structural formula which reads

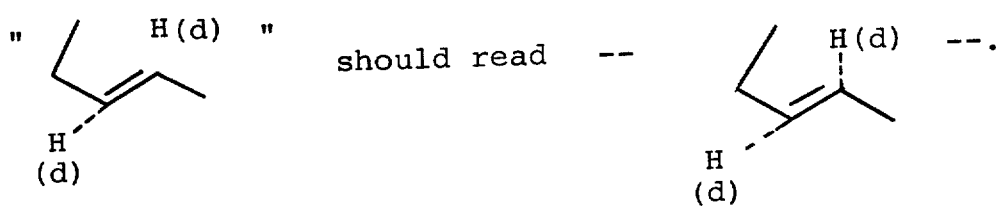

Column 8, line 29: "(h): 3.67 mto" should read -- (h): 3.67 to --.

UNITED STATES PATENT AND TRADEMARK OFFICE
CERTIFICATE OF CORRECTION

PATENT NO. : 4,264,623
DATED : April 28, 1981
INVENTOR(S) : JEAN BUENDIA ET AL

It is certified that error appears in the above—identified patent and that said Letters Patent is hereby corrected as shown below:

Column 10, line 40: "carboxylic" should read --carboxylate--.

Column 13, second structure formula: The portion of that formula which reads:

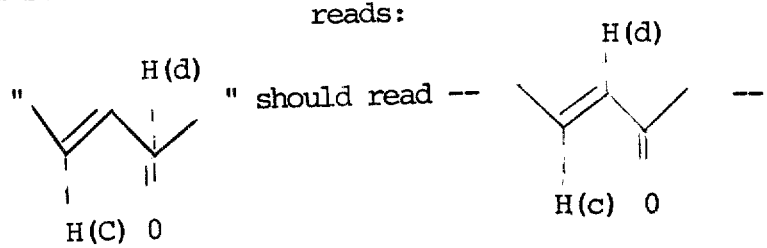

Column 14: The portion of the structural formula which reads

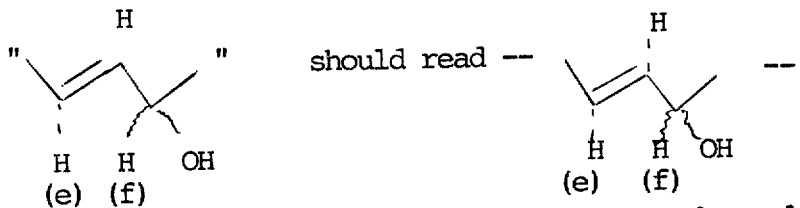

Signed and Sealed this

Fifteenth Day of December 1981

|SEAL|

Attest:

GERALD J. MOSSINGHOFF

Attesting Officer     Commissioner of Patents and Trademarks